United States Patent [19]

Daire et al.

[11] Patent Number: 5,440,930
[45] Date of Patent: Aug. 15, 1995

[54] ULTRASONIC MEASURING ASSEMBLY AND MEANS FOR ATTACHING SAME TO A VESSEL

[75] Inventors: Sylvie Daire, Chateauneuf les Martigues; Michel Demets, Istres, both of France

[73] Assignee: Elf Atochem S.A., Puteaux, France

[21] Appl. No.: 11,684

[22] Filed: Feb. 1, 1993

[30] Foreign Application Priority Data

Jan. 31, 1992 [FR] France ............... 92 01074

[51] Int. Cl.⁶ ............................ G01N 29/28
[52] U.S. Cl. ................... 73/644; 73/861.18; 73/866.5
[58] Field of Search ............ 73/632, 644, 861.18, 73/861.27, 861.28, 431, 866.5, DIG. 1

[56] References Cited

U.S. PATENT DOCUMENTS

| | | | |
|---|---|---|---|
| 4,019,373 | 4/1977 | Freeman et al. | 73/644 |
| 4,069,433 | 1/1978 | McShane | 310/325 |
| 4,287,755 | 9/1981 | Mansfield | 73/644 |
| 4,374,477 | 2/1983 | Kikuchi et al. | 73/861.18 |
| 4,454,767 | 6/1984 | Shinkai et al. | 73/861.18 |
| 4,556,813 | 12/1985 | Baumoel | 73/644 |
| 4,770,038 | 9/1988 | Zuckerwar et al. | 73/290 V |
| 4,779,452 | 10/1988 | Cohen-Tenoudji et al. | 73/54.41 |
| 4,783,997 | 11/1988 | Lynnworth | 73/644 |
| 4,872,345 | 10/1989 | Dicks | 73/597 |
| 4,948,552 | 8/1990 | Mollot et al. | 73/644 |
| 5,029,474 | 7/1991 | Schulze | 73/644 |

FOREIGN PATENT DOCUMENTS

56/133623  1/1982  Japan.

OTHER PUBLICATIONS

Text: "Kirk-Othmer Encyclopedia of Chemical Technology", 3rd Ed. Suppl. vol. Alcohol Fuels to Toxicology (489, 490).

Primary Examiner—Hezron E. Williams
Assistant Examiner—Rose M. Finley
Attorney, Agent, or Firm—Burns, Doane, Swecker & Mathis

[57] ABSTRACT

The flow rate of a high temperature fluid flowing through a conduit is measured by passing ultrasonic waves through the fluid. The ultrasonic waves are emitted from an emitter located at one side of the conduit and are received by a receiver located at an opposite site thereof. A first spacer is disposed between the receiver and the conduit, and a second spacer is disposed between the emitter and the conduit. The spacers isolate the receiver and emitter from the high temperatures and conduct the ultrasonic waves without changing the frequency thereof. A quick-release clamp clamps the emitter, receiver and spacers together against the conduit.

14 Claims, 2 Drawing Sheets

ULTRASONIC MEASURING ASSEMBLY AND MEANS FOR ATTACHING SAME TO A VESSEL

BACKGROUND OF THE INVENTION

The present invention relates to a device for fixing an ultrasonic probe to a vessel.

Ultrasonic probes are used for measuring various parameters of a medium, e.g., flow rates, levels, thicknesses, and for detecting impurities.

All these probes have a maximum working temperature either to avoid their destruction or for the reliability and reproducibility of the measurement.

An ultrasonic device for measuring the height of a liquid contained in a vessel such as a pressurized tank is described in U.S. Pat. No. 4,770,038. A plug is screwed through the side of the tank, and a piezoelectric element is disposed within the plug. It is indicated that the piezoelectric element may be fitted with cooling means, but without specifying the nature thereof.

U.S. Pat. No. 4,872,345 describes the use of an ultrasonic probe for monitoring the thickness of a refractory lining covering the internal wall of a vessel such as a high-temperature synthesis reactor. This probe, of tubular shape, passes through the wall of the reactor and its refractory lining. At the inner end of the tube there is fixed an ultrasonic transmitter, and at the outer end of the tube are disposed cooling fins.

U.S. Pat. No. 4,779,452 describes an ultrasonic viscosimeter for monitoring the viscosity of a resin disposed in a vessel such as an autoclave. An ultrasonic transmitter is fixed onto one of two buffers which are arranged one on top of the other. The transmitter is fixed to the first buffer by a tin/silver alloy. The second buffer, preferably made of aluminum, is covered with copper by electrolysis in order to be welded more easily to the first buffer which is preferably made of copper. The viscosimeter projects into the autoclave. The echo generated at the interface of the two buffers and that generated at the interface with the resin are processed by a computer in order to determine the viscosity.

U.S. Pat. No. 4,287,755 describes an ultrasonic device for treating molten aluminum. The device includes a water-cooled probe which projects into the aluminum.

Ultrasonic probes have also been used to measure flow rates of high temperature fluids disposed in vessels such as conduits. This technique is described in KIRKOTHMER Encyclopedia of Chemical Technology, 3rd edition, supplement vol. pages 489-490. An emitter is arranged against the external wall of a pipe. The receiver is arranged diametrically opposite to the emitter.

One shortcoming of the above-described arrangements is that the probes are of complicated design and cannot be quickly disassembled and disconnected from the member to which it is attached. Hence, considerable time and effort is required if it is desired to take measurements at various locations by the same probe.

It would be desirable to provide a more easily dissemblable ultrasonic probe arrangement which protects the ultrasonic elements (i.e., the receiver and emitter) from the heat of the medium being measured.

SUMMARY OF A PREFERRED EMBODIMENT OF THE INVENTION

A much simpler device has now been developed, which can be disassembled rapidly in order to be used at another measurement point.

The device includes a spacer provided with means for fixing it against the external wall of a vessel containing a fluid at high temperature. Against the spacer is fixed an ultrasonic element, such as an emitter or receiver, such that the spacer is disposed between the vessel wall and the emitter or receiver. Hence, the beam of waves must pass through the spacer. The spacer may be of any shape or material provided that it can transmit the beam of waves without the frequency thereof being altered.

The spacer may be in the shape of a cube with edges a few centimeters long.

The spacer may be fixed by screws or any means against the vessel wall, it being sufficient to provide fasteners, or lugs. The spacer can be easily fixed to the wall, and can be disassembled rapidly. It is also possible to arrange several spacers fixed at different locations and to have only an emitter or receiver, or a combination of an emitter and a receiver. In fact, an advantage of this spacer is that the emitter or the receiver can be fixed thereto rapidly and removed a few minutes later in order to be used at another location on another spacer.

The material of the spacer may be heat-conducting or non-heat-conducting. If an insulating (non-heat conducting) material is chosen, a person skilled in the art will determine the dimensions of the spacer such that the emitter or the receiver is sufficiently insulated from the hot vessel wall. Glass may for example be used.

If a thermal conducting material is chosen, it is provided with a heat exchange structure.

The heat exchange structure may be of any shape, for example, an aluminum cylinder may be machined so that deep grooves are formed on the outside periphery in order to provide air cooling fins in the form of discs oriented perpendicular to the axis of the cylinder. Then, one of the ends of this cylinder is hollowed out in order to make a cavity intended to receive the emitter or the receiver. The heat exchanger thus formed has its non-hollowed side placed flat against the wall of the vessel, it being possible for the axis of the cylinder to be perpendicular to the wall. The emitter or the receiver is arranged in the hollowed part of the cylinder. The advantage of the heat exchanger is that it can conduct and dissipate heat.

The person skilled in the art may choose a spacer shaped and material which is appropriate for the various probes and for the various wall temperatures.

It is possible to connect the two spacers together by means which clamps both spacers against the vessel. The two spacers can be connected by threaded rods, cables, and straps. If the emitter and the receiver were in the same plane passing through the axis of the pipe without being diametrically opposite, but situated on either side of the pipe, this would not depart from the scope of the invention.

DESCRIPTION OF THE DRAWINGS

The objects and advantages of the invention will become apparent from the following detailed description of a preferred embodiment thereof in connection with the accompanying drawings, in which like numerals designate like elements, and in which.

DETAILED DESCRIPTION OF A PREFERRED EMBODIMENT OF THE INVENTION

Figure 1:
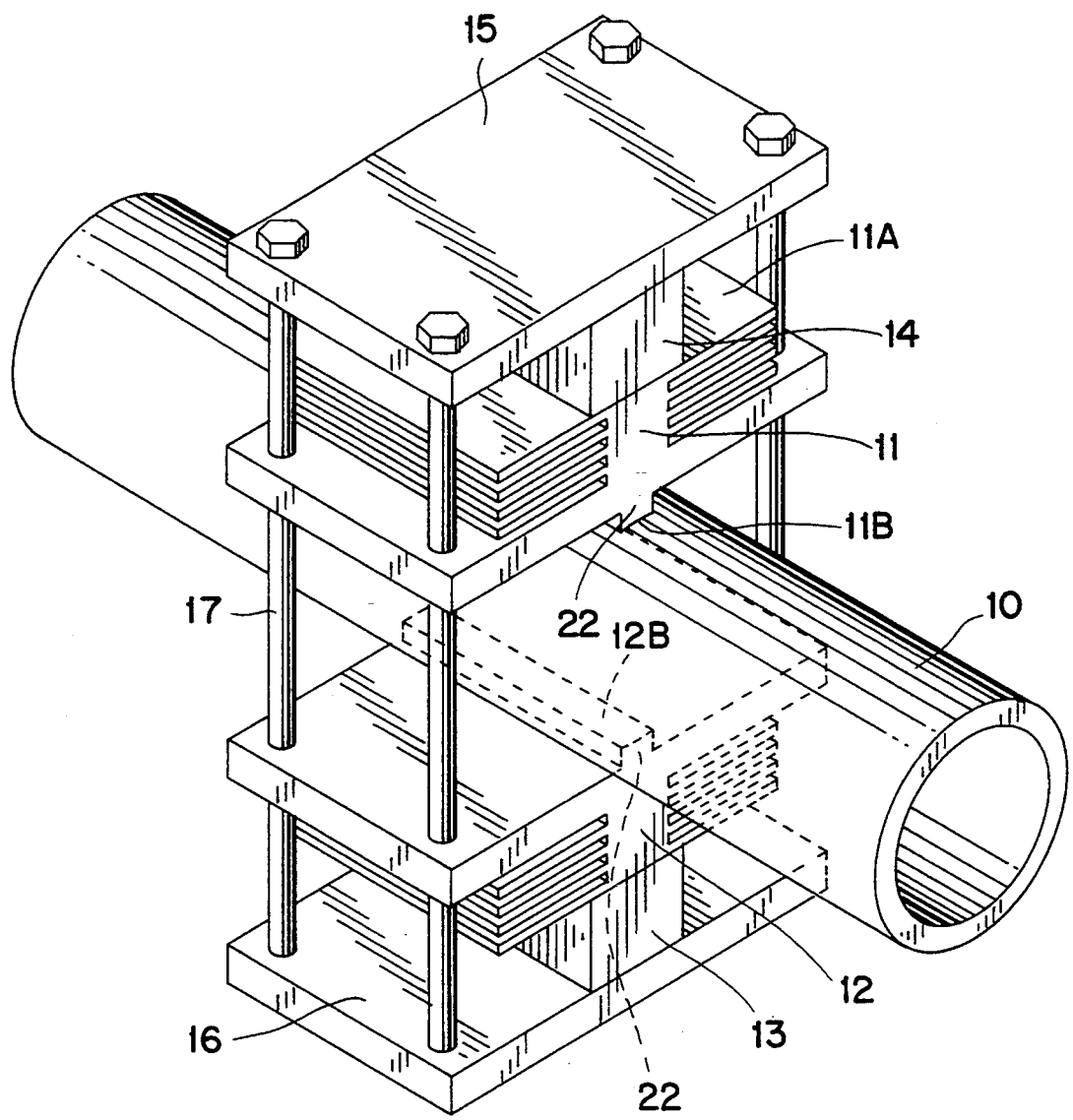
FIG. 1 is a perspective view of an apparatus according to the present invention clamped to a conduit.
Figure 2:
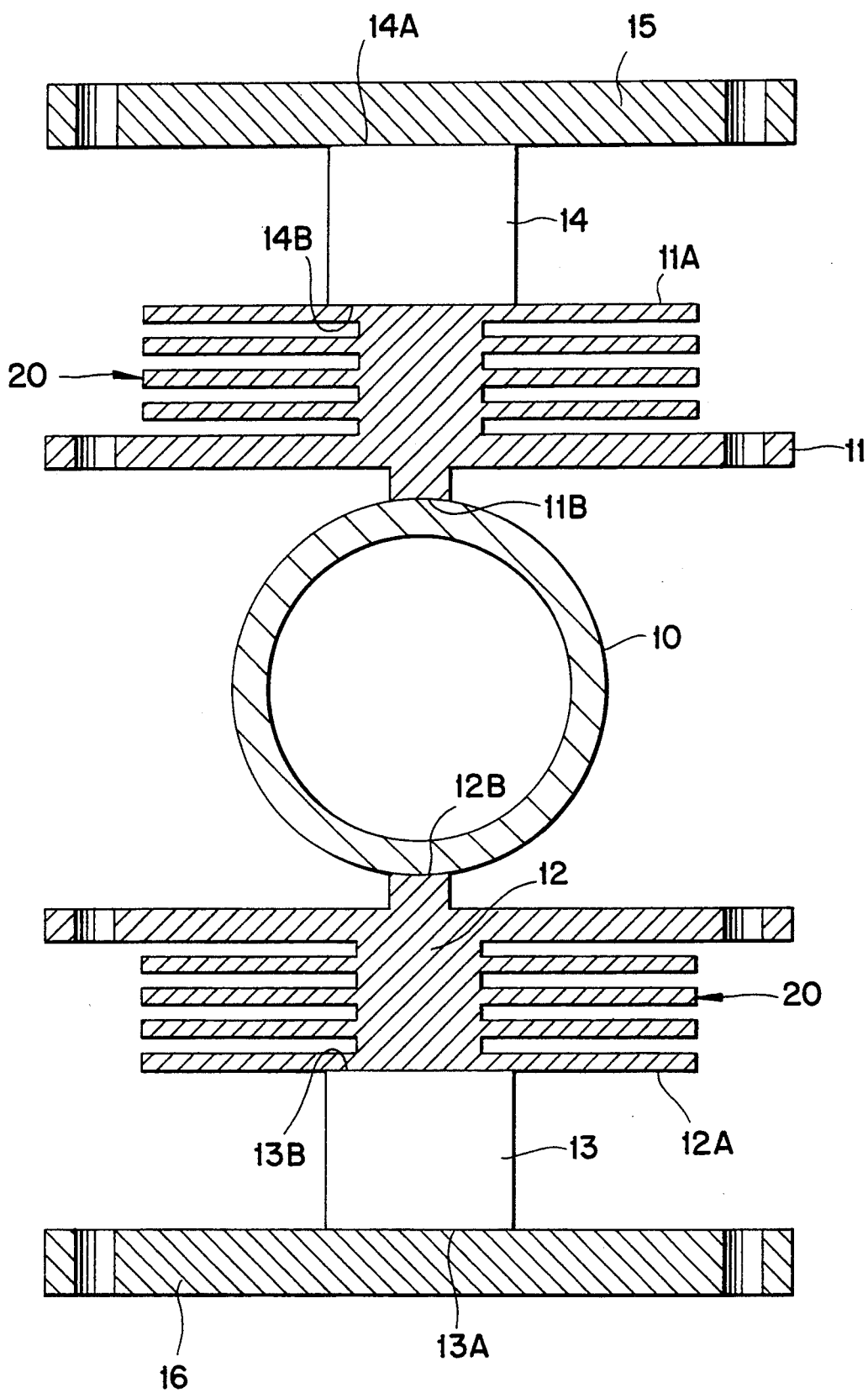
FIG. 2 is a vertical sectional view taken through the apparatus shown in FIG. 1.

FIG. 1 depicts an apparatus for measuring the flow rate of a high temperature fluid flowing in a vessel in the form of a tubular conduit 10. First and second spacer elements 11, 12 bear against opposite sides of the conduit 10. Each spacer is formed of a material capable of transmitting ultrasonic waves without changing the frequency thereof, e.g., glass or aluminum for example.

An ultrasonic wave receiver 14 engages an outer surface 11A of the first spacer 11, which surface 11A is disposed opposite an inner surface 11B of the spacer engaging an external surface of the conduit wall.

An ultrasonic wave emitter 13 engages an outer surface 12A of the second spacer 12, which surface 12A is disposed opposite an inner surface 12B of the spacer 12 engaging an external surface of the conduit wall. The emitter 13 emits ultrasonic waves which pass sequentially through the second spacer 12, the conduit wall of the fluid, the conduit wall, and the first spacer 11 before being received by the receiver.

A quick release clamping arrangement is provided for clamping the spacers 11, 12 against the conduit, and simultaneously clamping the emitter 13 and receiver 14 against the respective spacers 11, 12. The clamping mechanism comprises two clamp plates 15, 16 which engage outer surfaces 13A, 14A of the receiver and the emitter, respectively. The outer surfaces 13A, 14A are situated opposite inner surfaces 13B, 14B thereof which engage the respective spacers.

Clamping bolts 17 pass through the clamp plates 15, 16 and the spacers 11, 12 for drawing the clamp plates 15, 16 toward one another.

If the spacers 11, 12 are formed of a thermally conductive material, such as aluminum, thin air cooling fins 20 are formed on the outer periphery thereof. If the spacers are formed of a thermally insulative material, e.g., glass, then such fins would not be provided.

The surfaces 11B, 12B of the spacers which engage the conduit comprise concave surfaces formed on ribs 22 which project from the spacers.

It is possible to obtain reliable and reproducible measurements despite a loss of energy in the spacers provided that the frequency of the ultrasonic frequency is not changed.

Example

A device according to the invention was used for measuring, in a pipe of 60 mm external diameter, 6 mm thickness, the flow rate of a liquid phase essentially composed of 1,2-dichloroethane, heavy organic fractions and coke. The emitter and the receiver were probes of brand POLYSONICS model MST-P.

These probes do not withstand more than 150° C. The spacers 11 and 12 were of 25 mm thickness and the axes of the threaded rods 17 formed a rectangle of 105×50 mm.

The temperature of the external wall of the pipe measured by infrared means was 180° C., the temperature in the region of the probes measured by infrared means was 85° C.

The spacers effectively isolated the emitter and receiver from the high temperature of the conduit. Accurate measurements were conducted, because the spacers transmitted the ultrasonic waves without changing the frequency thereof.

The emitter and/or receiver could be quickly removed from the location on the conduit by simply loosening the bolts 17. The removed emitter and/or receiver could then be used elsewhere.

The device according to the invention is also useful for lagged pipes, it being sufficient to provide an opening in the lagging in order to fix a spacer having a thickness substantially equal to the lagging thickness or of a thickness allowing the emitter or the receiver to be fixed.

Although the present invention has been described in connection with preferred embodiments thereof, it will be appreciated by those skilled in the art that addition, deletions, modifications, and substitutions not specifically described may be made without departing from the spirit and scope of the invention as defined in the appended claims.

What is claimed is:

1. Apparatus for use in the measurement of a characteristic of a high temperature medium disposed in a vessel, wherein ultrasonic waves are passed through the medium, said apparatus comprising:
   a spacer element formed of a material for transmitting ultrasonic waves without changing the frequency thereof, said spacer element including opposing inner and outer opposing surfaces, said inner surface bearing against an external surface of a wall of the vessel;
   an ultrasonic element including opposing inner and outer surfaces, said inner surface bearing against said outer surface of said spacer element; and
   releasable fastening means applying an inwardly directed force to said outer surface of said ultrasonic element which is transmitted by said ultrasonic element to said outer surface of said spacer element for holding said inner end of said spacer against said external wall of said vessel.

2. Apparatus according to claim 1, wherein said fastening means comprises a clamp arrangement which clamps the spacer element against the external surface of the vessel wall and simultaneously clamps said ultrasonic element against said spacer element.

3. Apparatus according to claim 1 wherein said spacer element is formed of a thermally insulative material.

4. Apparatus according to claim 1 wherein said spacer element is formed of a thermally conductive material and includes cooling means.

5. Apparatus according to claim 4 wherein said cooling means comprises cooling fins.

6. Apparatus according to claim 1 wherein said ultrasonic element constitutes an ultrasonic wave emitter.

7. Apparatus according to claim 1 wherein said ultrasonic element constitutes an ultrasonic wave receiver.

8. Apparatus according to claim 1 wherein said spacer element constitutes a first spacer element; and said ultrasonic element constitutes a first ultrasonic element; said apparatus further comprising a second spacer element and a second ultrasonic element disposed on a side of said vessel wall situated opposite both said first spacer element and said first ultrasonic element; said second spacer element bearing against said vessel wall; said second ultrasonic element disposed on a side of said second spacer element situated opposite the side thereof which bears against said vessel wall, said first and second ultrasonic elements comprising an ultrasonic wave emitter and an ultrasonic wave receiver, respectively.

9. Apparatus according to claim 8 wherein said fastening means comprises first and second clamping plates and bolts for drawing said first and second clamping plates together, said first and second plates bearing against said first and second elements, respectively.

10. Apparatus for use in the measurement of a characteristic of a high temperature medium disposed in a vessel by passing ultrasonic waves through the medium, said apparatus comprising:

first and second spacer elements engaging generally opposite external sides of the vessel, each spacer element formed of a material capable of transmitting ultrasonic waves without changing the frequency thereof;

an ultrasonic wave receiver engaging a surface of said first spacer element disposed opposite a surface thereof which engages a vessel wall;

an ultrasonic wave emitter engaging a surface of said second spacer element disposed opposite a surface thereof which engages the vessel wall, said emitter positioned for emitting ultrasonic waves which pass sequentially through said second spacer element, one side of said vessel wall, said medium, another side of said vessel wall, and said first spacer element before being received by said receiver; and quick release clamping means clamping said emitter and said receiver to respective spacer elements, said clamping means comprising two clamp plates engaging outer surfaces of said emitter and receiver, respectively, and means for drawing said clamp plates toward one another.

11. Apparatus according to claim 10 wherein said means for drawing said clamp plates toward one another comprise bolts passing through said clamp plates.

12. Apparatus according to claim 11 wherein said bolts also pass through said first and second spacer elements.

13. Apparatus according to claim 10 wherein said first and second spacer elements include cooling fins.

14. Apparatus according to claim 10 wherein said vessel comprises a cylindrical conduit.

* * * * *